United States Patent
El-Sheikhy et al.

(10) Patent No.: US 9,625,438 B1
(45) Date of Patent: Apr. 18, 2017

(54) DEVICE FOR MEASURING EXPANSIVE SOIL SHRINKAGE

(71) Applicant: KING SAUD UNIVERSITY, Riyadh (SA)

(72) Inventors: Refat Ahmed Ibrahim El-Sheikhy, Riyadh (SA); Mosleh Ali Al-Shamrani, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/345,409

(22) Filed: Nov. 7, 2016

(51) Int. Cl.
*G01N 33/24* (2006.01)
*G01B 21/02* (2006.01)

(52) U.S. Cl.
CPC .......... *G01N 33/246* (2013.01); *G01B 21/02* (2013.01)

(58) Field of Classification Search
None
See application file for complete search history.

(56) References Cited

U.S. PATENT DOCUMENTS

| 6,234,008 B1 | 5/2001 | Sjoblom et al. |
| 2014/0123738 A1 | 5/2014 | Bellier et al. |

FOREIGN PATENT DOCUMENTS

| CN | 102735800 A | 10/2012 |
| CN | 202631513 U | 12/2012 |
| CN | 104359789 A | 2/2015 |
| CN | 204613034 U | 9/2015 |

OTHER PUBLICATIONS

MacIver et al., "Laboratory Soils Testing," *Engineer Manual*, The Department of the Army, Nov. 30, 1970, pp. 3.

*Primary Examiner* — Paul West
*Assistant Examiner* — Xin Zhong
(74) *Attorney, Agent, or Firm* — Richard C. Litman

(57) ABSTRACT

The device for measuring expansive soil shrinkage includes a plurality of molds, a plate positioned beneath each mold, and a scale. The scale includes a primary plate having a center portion including an aperture and a secondary plate. The primary plate is positioned on top of the secondary plate. The scale also includes a plurality of primary supports, each primary support being positioned between the primary plate and the secondary plate, as well as a first arm movably positioned on the primary plate and a second arm movably positioned on the primary plate, the first arm and the second arm being connected to one another by a plurality of test wires. Further, the scale includes a plurality of cantilever arms movably positioned on the primary plate. The cantilever arms are configured for supporting one of the molds on the test wires.

8 Claims, 7 Drawing Sheets

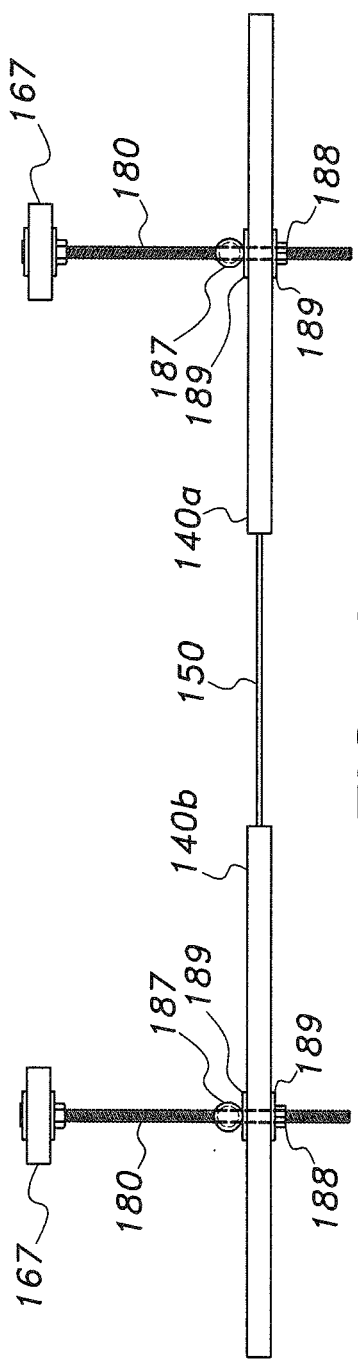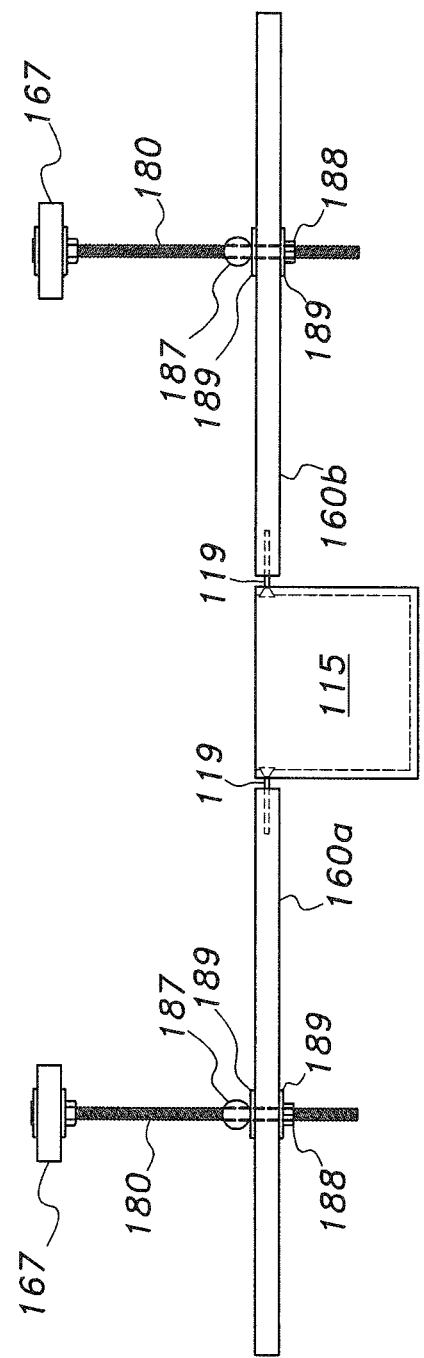

DEVICE FOR MEASURING EXPANSIVE SOIL SHRINKAGE

BACKGROUND OF THE INVENTION

1. Field of the Invention

The present invention relates to devices for measuring the properties of soil, and particularly to a device for measuring expansive soil shrinkage.

2. Description of the Related Art

The swelling-shrinkage capacity of soil refers to the extent that soil containing clay minerals will expand (i.e., swell) when wet and contract (i.e., shrink) when dry. The amounts of certain clay minerals present in the soil tend to directly affect the swelling-shrinkage capacity of soil. Soil with a high swelling-shrinkage capacity is problematic and is known as expansive soil. The ability to drastically change volume can cause damage to existing structures, such as cracks in housing foundations or the walls of swimming pools.

The swelling of expansive soil is usually measured experimentally only in laboratories by using odometers or tri-axial devices. These systems allow only for measuring the swelling under the effect of water pressure and air suction surrounding the sample. In other words, the swelling mechanism is artificially simulated by using disturbed soils samples. These samples, however, typically cannot represent the soil in nature, especially since the soil microstructure and the compaction factor are completely different than what exists in nature. Additionally, these systems not only take a long time to carry out the experiment and get results, but also cannot be done in the field. The time required to carry out one experiment takes approximately one month. Further, the systems measuring the swelling behavior of soil cannot simultaneously test the shrinkage behavior of the expansive soil. As such, existing systems can only measure the swelling behavior of expansive soil, which cannot represent the cyclic behavior between swelling and shrinkage of expansive soil.

Thus, a device for measuring expansive soil shrinkage solving the aforementioned problems is desired.

SUMMARY OF THE INVENTION

The device for measuring expansive soil shrinkage includes a plurality of molds, a plate positioned beneath each mold, and a scale. The scale includes a primary plate and a secondary plate, the primary plate having a center portion including an aperture. The primary plate is positioned on top of the secondary plate. The scale also includes a plurality of primary supports, each primary support being positioned between the primary plate and the secondary plate, as well as first and second arms movably positioned on the primary plate, the first arm and the second arm being connected to one another by a plurality of test wires. Further, the scale includes a plurality of cantilever arms movably positioned on the primary plate. Both cantilever arms acting in concert are configured for supporting one of the molds on the test wires.

These and other features of the present invention will become readily apparent upon further review of the following specification and drawings.

BRIEF DESCRIPTION OF THE DRAWINGS

FIG. 7A: is a side view of a first arm and a second arm used in conjunction with the device for measuring expansive soil shrinkage according to the present invention.

FIG. 7B: is a side view of a first cantilever arm and a second cantilever arm used in conjunction with the device for measuring expansive soil shrinkage according to the present invention.

Similar reference characters denote corresponding features consistently throughout the attached drawings.

DETAILED DESCRIPTION OF THE PREFERRED EMBODIMENTS

Figure 1:
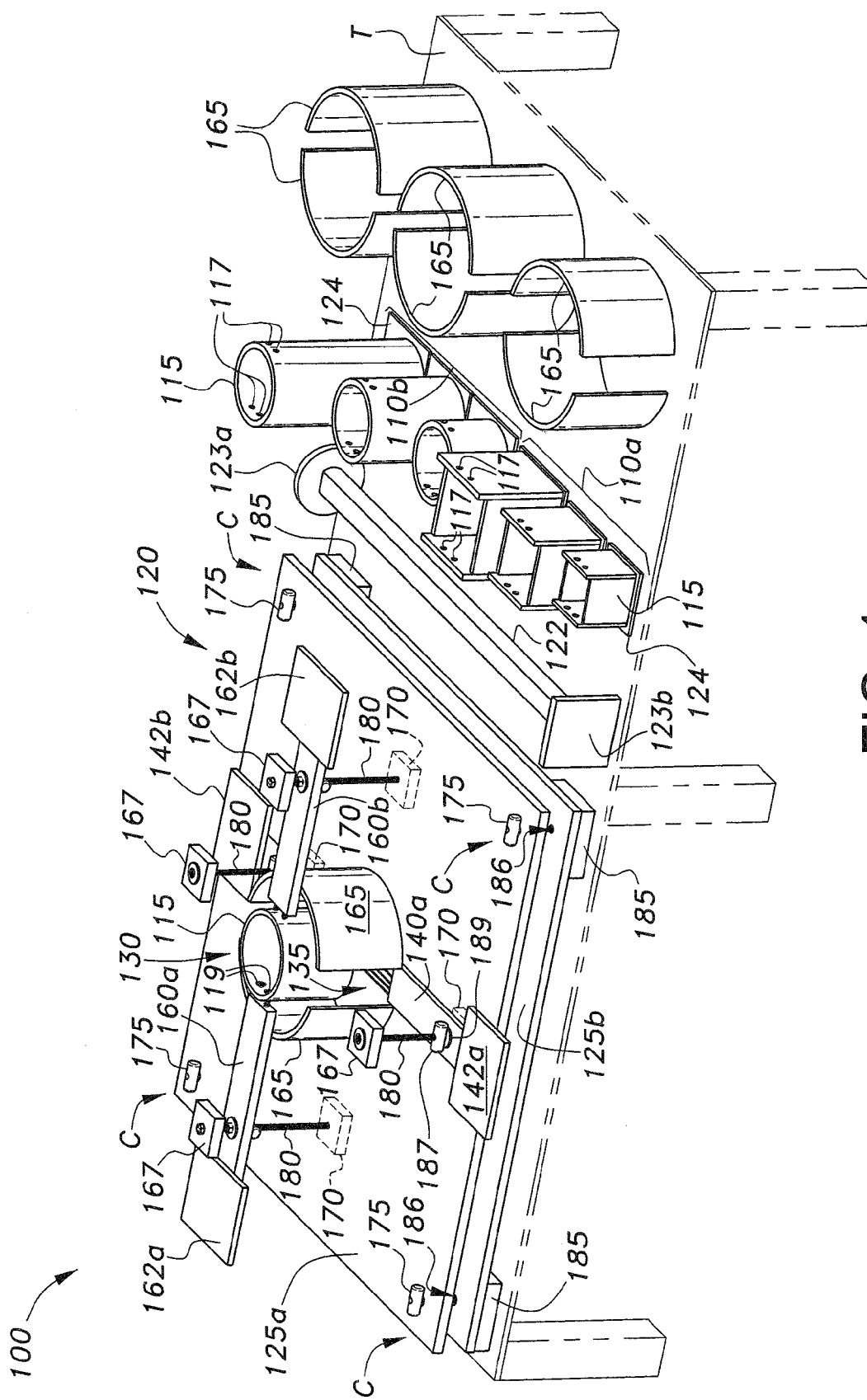
FIG. 1: is a perspective view of a device for measuring expansive soil shrinkage according to the present invention.
Figures 2A, 2B:
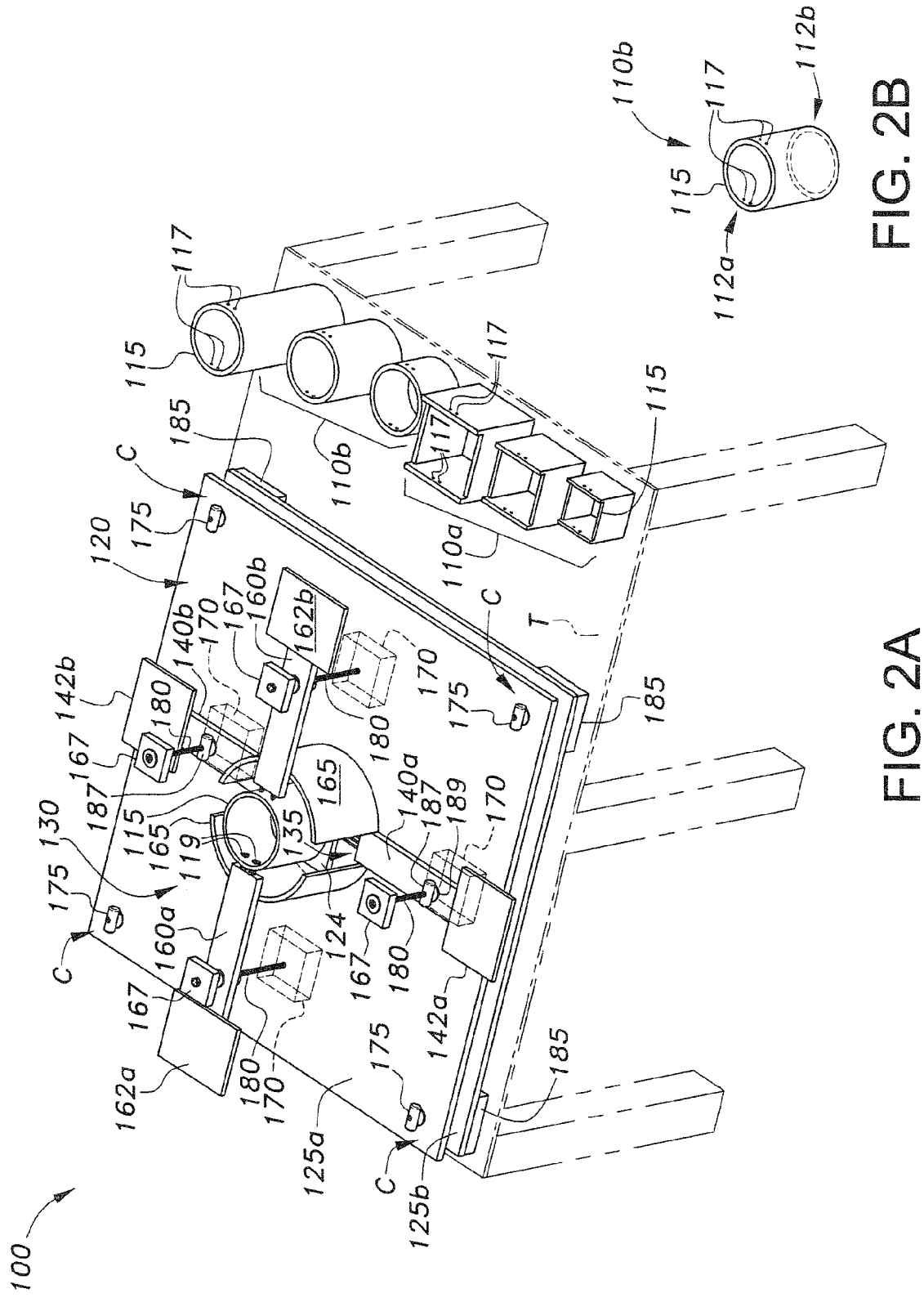
FIG. 2A: is a top perspective view of the device for measuring expansive soil shrinkage according to the present invention.
FIG. 2B: illustrates a mold for a device for measuring expansive soil shrinkage according to the present invention.
Figure 3:
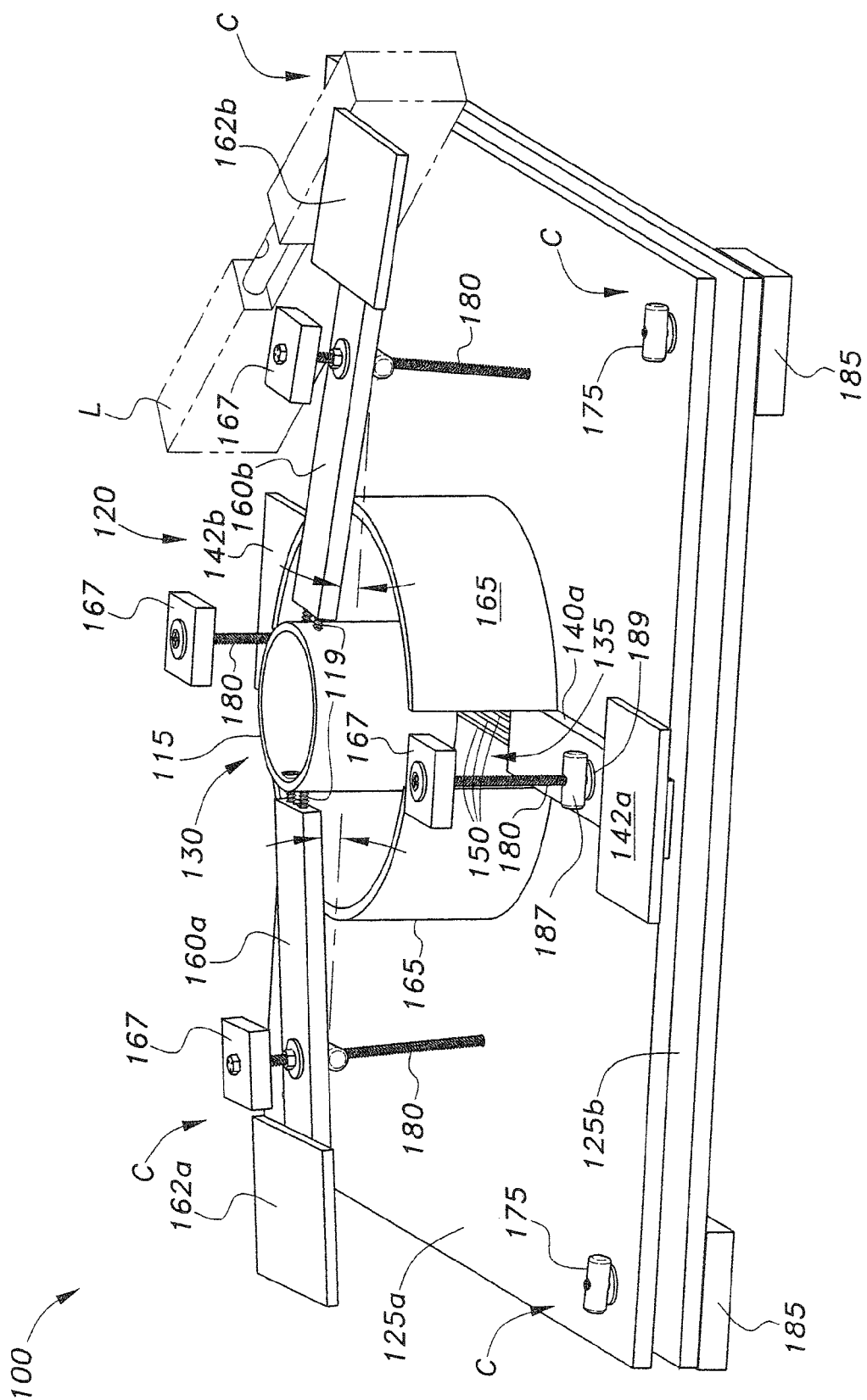
FIG. 3: is another perspective view of a device for measuring expansive soil shrinkage according to the present invention.
Figure 4:
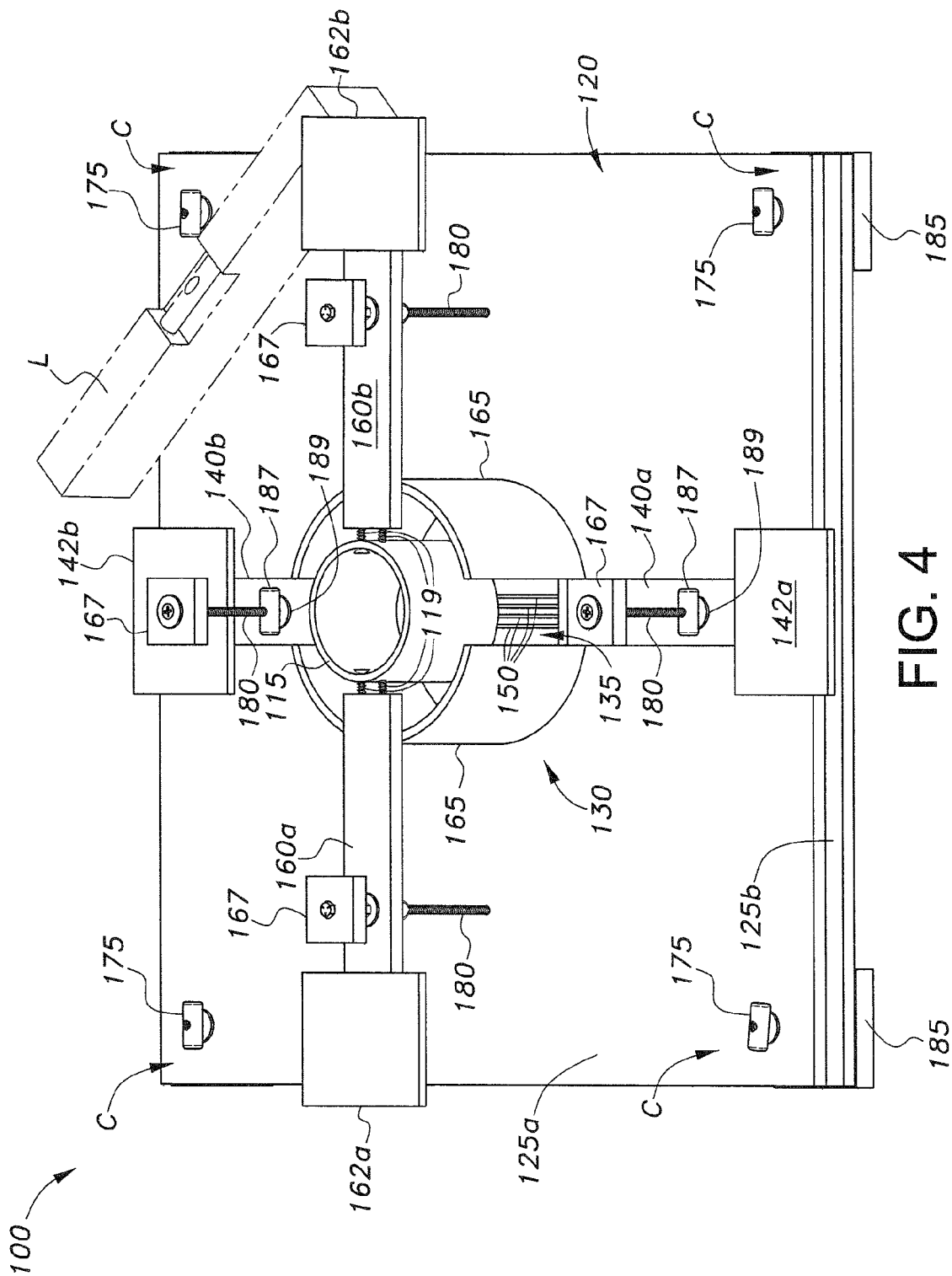
FIG. 4: is another top perspective view of the device for measuring expansive soil shrinkage according to the present invention.
Figure 5:
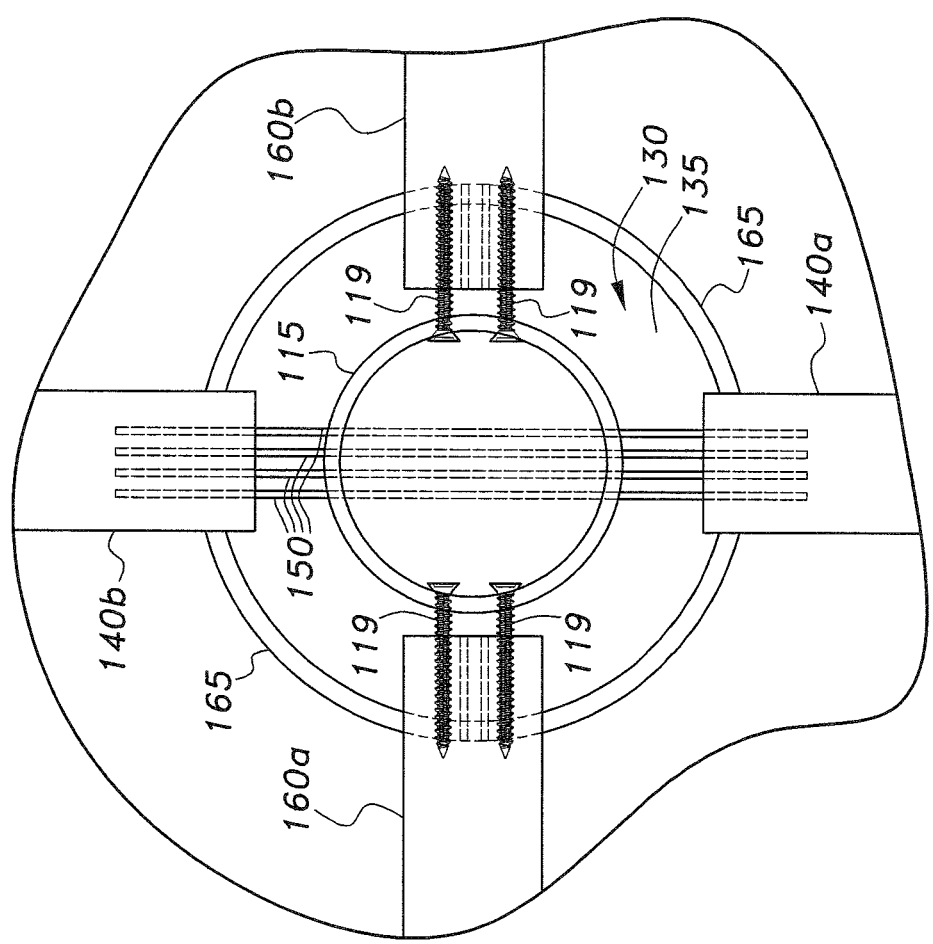
FIG. 5: is a detailed top view of a center portion of the device for measuring expansive soil shrinkage according to the present invention.
Figure 6:
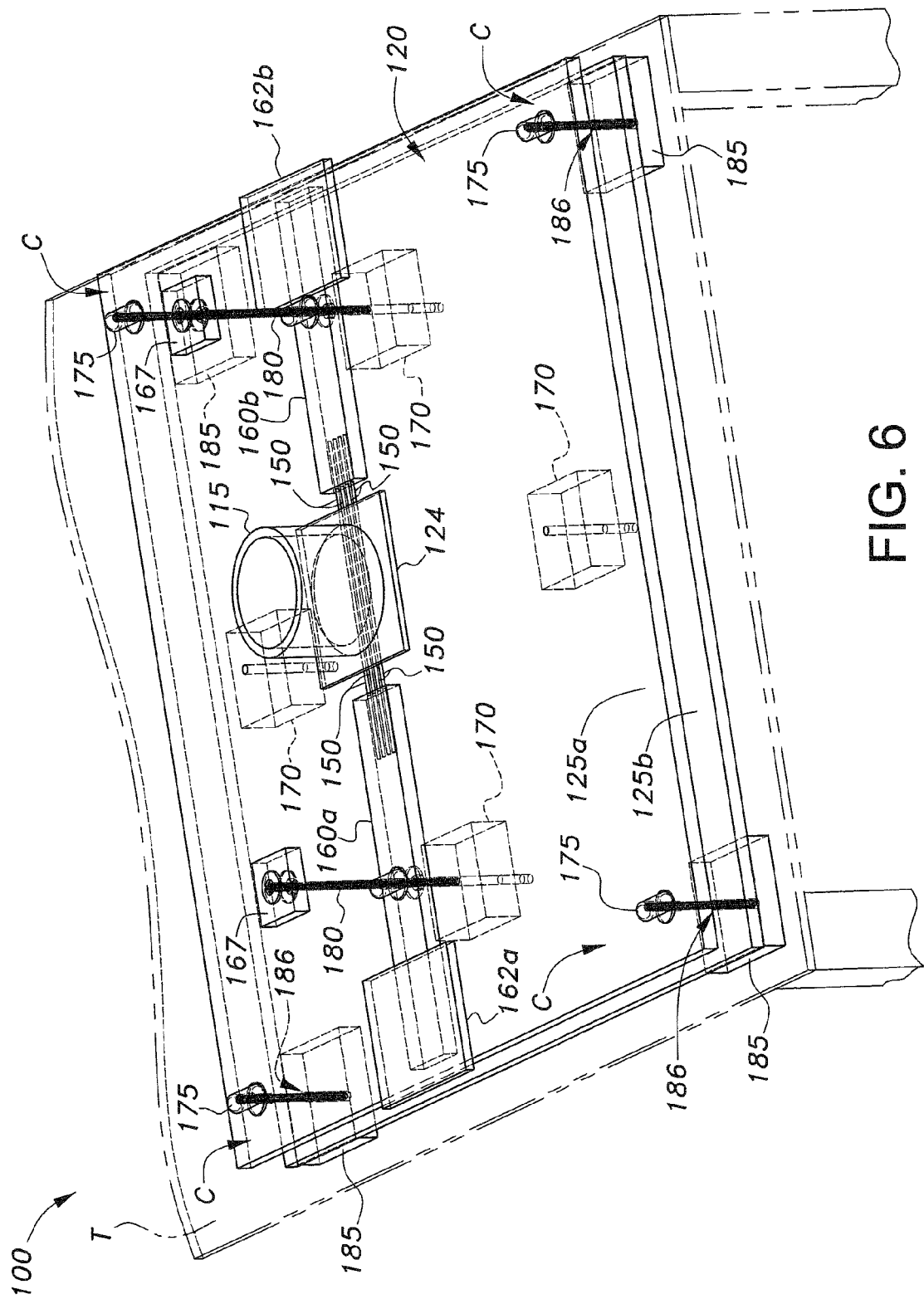
FIG. 6: is a perspective view of the device for measuring expansive soil shrinkage according to the present invention.

Referring to FIGS. 1-7B, a device 100 for measuring expansive soil shrinkage under environmental conditions (e.g., temperature, humidity, and pressure of the surrounding environment) is generally illustrated. The device 100 can be used in the field or in a laboratory, such as on a table T. The device 100 depends on the rapid check of the swelling/shrinkage movements in the field or in the laboratory to know if the soil is expansive or not, as well as the degree of swelling and shrinkage. Additionally, the device can aid in determining the presence of nano-clay, as well as the ratio of nano-clay to soil in the soil being examined. The monitoring of the actual behavior of the shrinkage mechanism of the soil samples can be done by using one's eyes or a microscope, which may be an electron microscope or an optical microscope. The soil samples can also be monitored using cameras, which may be normal cameras, high speed cameras, or thermal cameras. The device 100 may be connected to a computer or other suitable data acquisition system. Further, the device 100 may include sensors, such as piezoelectric sensors, to measure soil sample deformations under free shrinkage behavior. If the device 100 is connected to a computer, strain gauges can be embedded in the soil sample to measure the strains of the soil sample, the strain gauges being connected to computer(s) or other suitable data acquisition system.

The device 100 includes a plurality of molds, generally illustrated as 115, configured for holding a soil sample, each mold 115 having a corresponding plate 124 positioned beneath the mold 115, and a scale 120. The plate 124 is configured for preventing soil from escaping once the mold 115 is arranged in a vertical position. The scale 120 includes a primary plate 125a having a center portion 130 including an aperture 135, e.g., a circular aperture, and a secondary plate 125b, the primary plate 125a being positioned on top of the secondary plate 125b. A plurality of walls 165 (preferably two walls 165) having a semi-circular shape may be removably positioned on the primary plate 125a to partially surround the aperture 135 in the center portion 130 of the primary plate 125a and protect the mold 115, once the mold 115 is positioned on the scale 100.

The scale 120 also includes a first arm 140a and an opposing second arm 140b. Both arms 140a, 140b are movably positioned on opposing sides of the aperture 135 of the primary plate 125a. A plurality of test wires 150 (FIG. 3) connects the first arm 140a with the opposing second arm 140b such that the test wires 150 are positioned above the aperture 135 of the primary plate 125a and are arranged to cross the aperture 135 from one side of the aperture 135 to the other side of the aperture 135. The test wires 150 are configured for supporting the mold 150. It is to be noted that the corresponding plate 124 is positioned beneath each of the test wires 150. The test wires 150 are configured for allowing the soil sample to shrink without friction at the bottom surface of the soil.

Further, the scale 120 includes a first cantilever arm 160a and an opposing second cantilever arm 160b configured for supporting the mold 115 on the test wires 150 during the testing of the soil sample, which is contained in the mold 115. Both cantilever arms 160a, 160b are movably positioned on the primary plate 125 on opposing sides of the aperture 135 of the primary plate 125a. It is to be noted that the first arm 140a and the opposing second arm 140b and the first cantilever arm 160a and the opposing second cantilever arm 160b are positioned on different opposing sides of the aperture 135.

A plurality of primary supports 170 (preferably four primary supports 170) are positioned between the primary plate 125a and the secondary plate 125b to allow air to pass through the primary plate 125a and the secondary plate 125b and make contact with the soil sample resting on the test wires 150 above the plate 124 to allow the soil sample to dry under ambient conditions, such as natural environmental conditions or artificial laboratory conditions. Each primary support 170 is configured for receiving threaded screw bolts 180 securing the first arm 140a, the opposing second arm 140b, the first cantilever arm 160a, and the opposing second cantilever arm 160a to the primary plate 125a. Each threaded screw bolt 180 includes a gripping member 167 configured for raising and lower the arms 140a, 140b and the cantilever arms 160, 160b, as described further below. The threaded screw bolt 180 is threaded through each arm 140a, 140b and each cantilever arm 160a, 160b and through the primary plate 125a and into each corresponding primary support 170.

The molds 115 can be formed from any suitable non-conductive, transparent material, such as plastic, that is strong, lightweight, and easily transportable. Each mold 115 can be arranged in a set, such as a set of cubical molds 110a or a set of cylindrical molds 110b, including a plurality of individual molds 115 (preferably three molds 115). Each mold 115 includes an open top portion 112a suitable for receiving the soil to be tested and an open bottom portion 112b.

The molds 115 further include a plurality of openings 117 (preferably a total of four openings 117), including two openings 117 positioned on one side of the mold 115 and another two openings 117 positioned on the opposing side of the mold 115. Each opening 117 is configured for receiving a fastener 119, such as a screw, configured for securing one end of the first cantilever arm 160a to one side of the mold 115 and one end of the opposing second cantilever arm 160b to the opposing side of the mold 115 to support the mold 115 when the mold 115 is positioned vertically on the plate 124, as well as to prevent each of the test wires 150 from bending while the soil being tested is positioned on the test wires 150.

Further, each of the walls 165 coupled to the primary plate 125a can provide additional support for each of the cantilever arms 160a, 160b to further prevent each of the test wires 150 from bending while the mold 115 containing the soil is positioned on the test wires 150.

It is to be noted that each mold 115 has a different size, such as small, medium, and large, to hold a different amount of soil. In other words, each mold 115 in the set of cubical molds 110a includes a given area, while each mold 115 in the set of cylindrical molds 110b includes a given diameter. A tool 122, such as a compaction tool, having a circular end 123a and a square end 123b can be used to pack the soil in the mold 115. For example, the circular end 123a can be used to pack the soil in the mold 115 having a cylindrical shape and the square end 123b can be used to pack soil in the mold 115 having a cubical shape. The tool 122 can also be used to aid in removing the mold 115 from the soil being sampled. For example, when the mold 115 is being lifted the tool 122 may be used to apply downward pressure on the soil so that the mold 115 can be lifted without accidentally removing any soil.

The primary plate 125a and the secondary plate 125b of the scale 100 can be formed from any suitable non-conductive, transparent material, such as plastic, that is strong, lightweight, and easily transportable. The primary plate 125a and the secondary plate 125b, further, can have any suitable shape, such as a generally square shape. The aperture 135 of the center portion 130 of the primary plate 125a includes a diameter greater than the given area of mold 115 in the set of cubical molds 110a and greater than the given diameter of each mold 115 in the set of cylindrical molds 110b, such that each mold 115 can rest on the test wires 150 connecting the first arm 140a and the opposing second arm 140b, as illustrated on FIGS. 3-5, without touching the primary plate 125a.

Each corner C of the primary plate 125a and the corresponding corner C of the secondary plate 125b is configured for receiving a threaded screw bolt 186, similar to the threaded screw bolt 180. Each corner C of the primary plate 125a must first be aligned with a corresponding corner C of the secondary plate 125b prior to inserting the threaded screw bolt 186 through the opening (not shown) in the corner C of the primary plate 125a and the opening (not shown) in the corresponding corner C of the secondary plate 125b. A plurality of secondary supports 185 (preferably four secondary supports 185) are movably positioned beneath the secondary plate 125b beneath each corner C of the secondary plate 125b to elevate the secondary plate 125b from the table T. Each of the secondary supports 185 is adapted for receiving the threaded screw bolt 186 passing through the corners C of primary plate 125a and the corresponding corners C of the secondary plate 125b. The threaded screw bolts 186 can be tightened by any suitable means, such as by barrel nuts 175. By rotating each threaded screw bolt 186 in a direction, such as in a clockwise or a counter clockwise direction, the primary plate 125a can move in an upward direction or a downward direction along the threaded screw bolt 180 in relation to secondary plate 125b to level the scale 100. A level L can also be used to ensure that the primary plate 125a of the scale 100 is leveled.

The first arm 140a and the second arm 140b can each be formed from any type of suitable non-conductive, transparent material, such as plastic, and have any suitable shape, such as a generally rectangular shape. The first arm 140a includes a corresponding plate 142a and the second arm 140b includes a corresponding plate 142b. The first arm 140a and the second arm 140b are each movably positioned on the primary plate 125a, such as by the threaded screw bolt 180. The first arm 140a and the second arm 140b are secured to the corresponding threaded screw bolt 180 by a barrel nut 187 and a nut 188, as illustrated in FIG. 7A. Washers 189 can be positioned between the barrel nut 187 and the corresponding arm 140a, 140b, as well as between the corresponding arms 140a, 140b and the nut 188. Despite being connected by test wires 150, the first arm 140a and the second arm 140b can be moved uniformly in an upward direction or in a downward direction along the corresponding threaded screw bolt 180 by rotating the gripping member 167 associated with each arm, 140a, 140b in a clockwise direction or in a counter clockwise direction.

The first cantilever arm 160a and the second cantilever arm 160b can each be formed from any type of suitable non-conductive, transparent material, such as plastic, and have any suitable shape, such as a generally rectangular shape. The first cantilever arm 160a includes a corresponding plate 162a and the opposing second cantilever arm 160b includes a corresponding plate 162b. Weight can be added to the each plate 162a, 162b to counteract heavier soil samples. Similar to the first arm 140a and the second arm 140b, each cantilever arm 160a, 160b is secured to the corresponding threaded screw bolt 180 by a barrel nut 187 and a nut 188, as illustrated in FIG. 7B. Washers 189 can be positioned between the barrel nut 187 and the corresponding cantilever arms 160a, 160b, as well as between each corresponding cantilever arm 160a, 160b and the nut 188. Further, the griping members 167 associated with each cantilever arm 160a, 160b can be used to raise and lower each cantilever arm 160a, 160b by rotating the corresponding gripping member 167 in a clockwise or a counterclockwise direction. By rotating the gripping members 167 in a clockwise direction or in a counterclockwise direction, the corresponding threaded screw bolts 180 will also rotate in the same direction; thereby either raising or lowering the cantilever arms 160a, 160b and, in turn, lifting the mold 115 from the plate 124 or lowering the mold 115 onto the plate 220.

When conducting the experiment using the device 100, a total of three soil samples should be used on three separate devices 100, as well as one soil sample as a reference and another soil sample for measuring parameters in at the same time. The parameters being tested include determining the water content, the cation-exchange capacity (CEC), the Zeta potential, the temperature inside the test sample, the temperature outside the test sample, the humidity around the test samples, as well as the atmospheric pressure around the test samples. The microstructure (e.g. chemical composition) of the soil samples can be examined using scanning electron microscopy (SEM), transmission electron microscopy (TEM), x-ray powered diffraction (XRD), and energy-dispersive x-ray spectroscopy (EDS).

To commence the experiment using the device 100, the first cantilever arm 160a and the opposing second cantilever arm 160b, must be connected to the selected mold 115 (e.g., the cubic mold or the cylindrical mold) to be used by the fasteners 119. The plate 124 is then positioned under the test wires 150 to prevent any soil from falling out from the open bottom portion 112b of the mold 115 and to allow the soil being sampled to rest on the test wires 150. Once the open bottom portion 112b is covered, the mold 115 may be filled with the soil that is to be examined. The soil must then be suitably packed within the mold 115, such as by the tool 122. Wax can be applied to the area where the mold 115 makes contact with the plate 124 to prevent any water from escaping, draining, or spilling through the bottom portion 112b of the mold 115. The mold 115 containing the soil is left positioned on the test wires 150 resting on the plate 124 for approximately twenty-four to seventy-two hours. Since the test wires 150 are configured for supporting the mold 150 and the corresponding plate 124 containing the soil sample to allow the soil to shrink without friction at the bottom surface of the soil, each test wire 150 may be covered in oil to facilitate the shrinkage, (i.e. the reduction of the dimensions) of the soil sample.

After the time has expired, the gripping member 167 associated each cantilever arm 160a, 160b connected to the mold 115 can be rotated in a clockwise direction to lift cantilever arms 160a, 160b along the corresponding threaded screw bolt 180 and, in turn, slowly remove the mold 115 from the soil being examined, thereby leaving the soil resting on the test wires 150 resting on the plate 124. The tool 122 can be used to aid in removing the mold 115 from the soil. Once the mold 155 has been removed, the gripping member 167 associated with each arm 140a, 140b can be rotated in a clockwise direction to lift the soil resting on the test wires 150 off of the plate 124 to expose the bottom portion of the soil to the surrounding air and atmosphere and allow free evaporation of water from all sides of the soil being examined under existing atmospheric conditions (e.g., room temperature or field temperature).

The dimensions of the soil being examined should be measured every day, beginning on the day the soil was put into the mold 115. High speed cameras should be used to monitor and observe the soil samples during the testing. Further, deformations and cracks should also be monitored during the testing. During the testing, at least once per day, the griping member 167 associated with each cantilever arm 160a, 160b should be rotated in a counterclockwise direction to lower the mold 115 back over the soil sample and onto the test wires 150 resting on the plate 124 in order to measure the changes, if any, in the soil sample's dimensions. After measuring the changes in the soil sample's dimensions, the mold 115 should be lifted again without disturbing the soil sample, as described above. The test will continue until the changes in the dimensions of the soil samples stop and the soil samples are completely dried under the effect of surrounding conditions in the field or the room. During the testing, the results should be plotted on a graph to study the mechanism of shrinkage as compared with the actual behavior of the soil during shrinkage.

After the soil shrinkage has been determined, the swelling of the soil samples should be simulated and studied. To test the swelling of the expansive soil, water should be added to the dried soil sample in the mold 115 after closing it at the bottom by wax, as described above. Once the dried soil sample has been sealed with wax, the same steps discussed above can be used to determine the swelling effect of the soil samples. By testing shrinkage, then swelling, then shrinkage several times, one can study the cyclic swelling-shrinkage behavior of the soil samples. This will not only help in studying the fatigue of the soil and structures due to cyclic swelling-shrinkage, but also help in studying full swelling-shrinkage or partial swelling-shrinkage to determine the range of the soil shrinkage and swelling. Further, soil treatments can be developed by results of the tests described above, such as introducing lime, polymers, or other suitable chemicals into the soil to decrease the shrinkage-swelling phenomenon of the soil.

It is to be noted that all the tests should be done without any electrical or hydraulic devices or connection thereto to avoid producing any electrical field or magnetic field close to the soil samples. Such electrical fields or magnetic fields may affect the microstructure of the soil or the swelling-shrinkage behavior, since the swelling-shrinkage phenomenon depends on the presence of the negative charges of the clay particles in the soil attracting the positive charges in the melted minerals in the water. For this reason, the components of the device 100 should be formed from non-conductive, transparent materials, such as plastic.

It is to be understood that the present invention is not limited to the embodiments described above, but encompasses any and all embodiments within the scope of the following claims.

We claim:

1. A device for measuring expansive soil shrinkage, comprising:
   a plurality of molds, each of the molds having a corresponding plate positioned beneath the mold; and
   a scale, including:
      a primary plate including a center portion having an aperture;
      a secondary plate, the primary plate being positioned on top of the secondary plate;
      a plurality of primary supports, each of the primary supports being positioned between the primary plate and the secondary plate;
      a first arm movably positioned in communication with the primary plate;
      a second arm movably positioned on the primary plate, the first arm and the second arm being movably positioned on opposing sides of the aperture of the primary plate;
      a plurality of test wires connecting the first arm and the second arm; and
      a plurality of cantilever arms, each of the cantilever arm being movably positioned on opposing sides of the aperture in the primary plate, the cantilever arms being configured for supporting one of the plurality of molds on the test wires.

2. The device for measuring expansive soil shrinkage according to claim 1, further comprising a tool having a circular end and a square shaped end, the tool being configured for packing the soil in the mold.

3. The device for measuring expansive soil shrinkage according to claim 2, wherein the tool comprises a compacting tool.

4. The device for measuring expansive soil shrinkage according to claim 1, wherein the scale further comprises a plurality of secondary supports, each of the secondary supports being movably positioned beneath the secondary plate.

5. The device for measuring expansive soil shrinkage according to claim 1, further comprising a plurality of walls, each of the walls being removably positioned on the primary plate, each wall being semicircular and configured for partially surrounding the aperture in the center portion of the primary plate to protect the mold.

6. The device for measuring expansive soil shrinkage according to claim 1, wherein each said mold includes a plurality of openings configured for receiving a fastener selectively securing each cantilever arm to the mold.

7. The device for measuring expansive soil shrinkage according to claim 1, wherein each said mold is cylindrical.

8. The device for measuring expansive soil shrinkage according to claim 1, wherein each said mold is cubical.

* * * * *